US012156501B2

(12) United States Patent
Brooks, II et al.

(10) Patent No.: US 12,156,501 B2
(45) Date of Patent: Dec. 3, 2024

(54) LETTUCE CULTIVAR ADEMPACK

(71) Applicant: SOUTHWEST GENETICS, LLC, Yuma, AZ (US)

(72) Inventors: Davie Lee Brooks, II, Yuma, AZ (US); Jon Cody Nickerson, Yuma, AZ (US)

(73) Assignee: Southwest Genetics, LLC, Yuma, AZ (US)

( * ) Notice: Subject to any disclaimer, the term of this patent is extended or adjusted under 35 U.S.C. 154(b) by 176 days.

(21) Appl. No.: 17/965,952

(22) Filed: Oct. 14, 2022

(65) Prior Publication Data

US 2024/0122139 A1   Apr. 18, 2024

(51) Int. Cl.
*A01H 6/14*    (2018.01)
*A01H 1/02*    (2006.01)

(52) U.S. Cl.
CPC ............ *A01H 6/1472* (2018.05); *A01H 1/02* (2013.01)

(58) Field of Classification Search
None
See application file for complete search history.

(56) References Cited

U.S. PATENT DOCUMENTS

| | | | |
|---|---|---|---|
| 5,304,719 | A | 4/1994 | Segebart |
| 5,367,109 | A | 11/1994 | Segebart |
| 5,523,520 | A | 6/1996 | Hunsperger et al. |
| 5,684,226 | A | 11/1997 | Sarreal |
| 5,850,009 | A | 12/1998 | Kevern |
| 5,968,830 | A | 10/1999 | Dan et al. |
| 8,716,551 | B2 | 5/2014 | Michel |
| 2023/0024205 | A1* | 1/2023 | Brooks, II ............ A01H 6/1472 |

OTHER PUBLICATIONS

Allard, R.W., "Breeding Self-Pollinated Plants", Principles of Plant Breeding, 2$^{nd}$ ed., John Wiley & Sons, Inc., 1999, pp. 175-197.
Altpeter, F., et al., "Advancing Crop Transformation in the Era of Genome Editing", *The Plant Cell*, 2016, 28:1510-1520.
Bassett, M.J., "The role of leaf shape in the inheritance of heading in lettuce (*Lactuca sativa* L.)", *J. Am. Soc. Hortic. Sci.*, 1975, 100(2):104-105.
Bennetzen, J.L. and Jones, J.D.G., edited by Setlow, J.K., "Approaches and progress in the molecular cloning of plant disease resistance genes", *Genetic Engineering*, 1992, 14:99-124.
DeBolle, M.F.C., et al., "Antimicrobial peptides from *Mirabilis jalapa* and *Amaranthus caudatus*: expression, processing, localization and biological activity in transgenic tobacco", *Plant Molecular Biology*, 1996, 31:993-1008.
DeVries, I.M. and van Raamsdonk, L.W.D., "Numerical morphological analysis of lettuce cultivars and species (*Lactuca* sect. *Lactuca*, Asteraceae)", *Plant Systematics and Evolution*, 1994, 193:125-141.
Eshed, Y. and Zamir, D., "Less-than-additive epistatic interactions of quantitative trait loci in tomato", *Genetics*, 1996, 143:1807-1817.
Jiang, G.L., "Molecular Markers and Marker-Assisted Breeding in Plants", Plant Breeding from Laboratories to Fields, InTech, 2013, pp. 45-83.
Kamburova, V.S., et al., "Genome Editing in Plants: An Overview of Tools and Applications", *Intl J. of Agronomy*, 2017, Article ID 7315351, 15 pages.
Kraft, T., Hansen, M., and Nilsson, N.O., "Linkage disequilibrium and fingerprinting in sugar beet", *Theor. Appl. Genet.*, 2000, 101:323-326.
Malzahn, A., et al., "Plant genome editing with TALEN and CRISPR", *Cell Biosci*, 2017, 7:21, 18 pages.
Michelmore, R., et al., "Transformation of lettuce (*Lactuca sativa*) mediated by *Agrobacterium tumefaciens*", *Plant Cell Reports*, 1987, 6:439-442.
Pang, S., et al., "Expression of a gene encoding a scorpion insectotoxin peptide in yeast, bacteria and plants", *Gene*, 1992, 116:165-172.
Ryder, E.J., "Lettuce genetics: Inheritance, linkage and epistasis", *J. Amer. Soc. Hort. Sci.*, 1992, 117(3):504-507.
Ryder, E.J., Kim, Z.H. and Waycott, W., "Inheritance and epistasis studies of chlorophyll deficiency in lettuce", *J. Amer. Soc. Hort. Sci.*, 1999, 124(6):636-640.
Teng, W.L., et al., "Rapid Regeneration of Lettuce from Suspension Culture", *HortScience*, 1992, 27(9):1030-1032.
Waycott, W. and Fort, S.B., "Differentiation of nearly identical germplasm accessions by a combination of molecular and morphologic analyses", *Genome*, 1994, 37(4):577-583.
Whitaker, T.W., Ryder, E.J. and Hills, O.A., "Lettuce production in the United States, Agriculture Handbook No. 221", Agricultural Research Service of the U.S.D.A., 1974, pp. 4-5.
Xinrun, Z. and Conner, A.J., "Genotypic effects on tissue culture response of lettuce cotyledons", *J. Genet. & Breed.*, 1992, 46:287-290.

* cited by examiner

*Primary Examiner* — Brent T Page
(74) *Attorney, Agent, or Firm* — Jondle & Associates, P.C.

(57) ABSTRACT

A lettuce cultivar, designated ADEMPACK, is disclosed. The invention relates to the seeds, plants, and plant parts of lettuce cultivar ADEMPACK and to methods for producing a lettuce plant by crossing the cultivar ADEMPACK with itself or another lettuce cultivar. The invention further relates to methods for producing a lettuce plant containing in its genetic material one or more transgenes and to the transgenic lettuce plants and plant parts produced by those methods. This invention also relates to lettuce cultivars or breeding cultivars and plant parts derived from lettuce cultivar ADEMPACK, to methods for producing other lettuce cultivars, lines or plant parts derived from lettuce cultivar ADEMPACK and to the lettuce plants, varieties, and their parts derived from the use of those methods. The invention further relates to hybrid lettuce seeds, plants, and plant parts produced by crossing cultivar ADEMPACK with another lettuce cultivar.

22 Claims, No Drawings

LETTUCE CULTIVAR ADEMPACK

BACKGROUND OF THE INVENTION

The present invention relates to a new romaine lettuce (*Lactuca sativa* L.) variety designated ADEMPACK. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Practically speaking, all cultivated forms of lettuce belong to the highly polymorphic species *Lactuca sativa* that is grown for its edible head and leaves. As a crop, lettuce is grown commercially wherever environmental conditions permit the production of an economically viable yield. Lettuce makes the world's most popular salad. In the United States, the principal growing regions for lettuce are California and Arizona; in 2017, California accounted for nearly 73 percent of U.S. lettuce production, followed by Arizona producing over 21 percent. According to the 2017 USDA Census of Agriculture, lettuce was produced on 342,965 acres, which was up 5.7% since 2012. The value of U.S. lettuce production in 2017 totaled over $4.2 billion, making lettuce the leading vegetable crop in terms of value. Fresh lettuce is available in the United States year-round although the greatest supply is from May through October. For planting purposes, the lettuce season is typically divided into three categories (i.e., early, mid, and late), with the coastal areas planting from January to August, and the desert regions planting from August to December. Fresh lettuce is consumed nearly exclusively as fresh, raw product and occasionally as a cooked vegetable.

*Lactuca sativa* is in the Cichoreae tribe of the Asteraceae (Compositae) family. Lettuce is related to chicory, sunflower, aster, dandelion, artichoke, and *chrysanthemum. L. sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce comes in many varieties, none of which form a head, and include the green leaf and green oak leaf varieties. Latin lettuce looks like a cross between romaine and butterhead. Stem lettuce has long, narrow leaves and thick, edible stems. Oilseed lettuce is a type grown for its large seeds that are pressed to obtain oil. Latin lettuce, stem lettuce, and oilseed lettuce are seldom seen in the United States.

Lettuce in general is an important and valuable vegetable crop. Therefore, it is desirable to develop new varieties of lettuce having novel and exceptional traits, such as a combination of outstanding agronomic characteristics and resistance to diseases.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel lettuce cultivar designated ADEMPACK. Also provided are lettuce plants having the physiological and morphological characteristics of lettuce cultivar ADEMPACK. This invention thus relates to the seeds of lettuce cultivar ADEMPACK, to the plants of lettuce cultivar ADEMPACK, and to methods for producing a lettuce plant produced by crossing the lettuce cultivar ADEMPACK with itself or another lettuce plant, to methods for producing a lettuce plant containing in its genetic material one or more transgenes, and to the transgenic lettuce plants produced by that method. This invention also relates to methods for producing other lettuce cultivars derived from lettuce cultivar ADEMPACK and to the lettuce cultivar derived by the use of those methods. This invention further relates to hybrid lettuce seeds and plants produced by crossing lettuce cultivar ADEMPACK with another lettuce variety.

In another aspect, the present invention provides regenerable cells for use in tissue culture of lettuce cultivar ADEMPACK. The tissue culture will preferably be capable of regenerating plants having essentially all of the physiological and morphological characteristics of the foregoing lettuce plant, and of regenerating plants having substantially the same genotype as the foregoing lettuce plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole flowers, stalks and seeds. Still further, the present invention provides lettuce plants regenerated from the tissue cultures of the invention.

The invention also relates to methods for producing a lettuce plant containing in its genetic material one or more transgenes and to the transgenic lettuce plant produced by those methods.

Another aspect of the current invention is a lettuce plant further comprising a single locus conversion. In one embodiment, the lettuce plant is defined as comprising the single locus conversion and otherwise capable of expressing all of the morphological and physiological characteristics of the lettuce cultivar ADEMPACK. In particular embodiments of the invention, the single locus conversion may comprise a transgenic gene which has been introduced by genetic transformation into the lettuce cultivar ADEMPACK or a progenitor thereof. A transgenic or non-transgenic single locus conversion can also be introduced by backcrossing, as is well known in the art. In still other embodiments of the invention, the single locus conversion may comprise a dominant or recessive allele. The locus conversion may confer potentially any trait upon the single locus converted plant, including herbicide resistance, insect or pest resistance, resistance to bacterial, fungal, or viral disease, modified fatty acid metabolism, modified carbohydrate metabolism, male fertility or sterility, improved nutritional quality, and industrial usage. The trait may be, for example, conferred by a naturally occurring gene introduced into the genome of the cultivar by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

The invention further relates to methods for genetically modifying a lettuce plant of the lettuce cultivar ADEMPACK and to the modified lettuce plant produced by those methods. The genetic modification methods may include, but are not limited to mutation, genome editing, RNA interference, gene silencing, backcross conversion, genetic transformation, single and multiple gene conversion, and/or direct gene transfer. The invention further relates to a genetically modified lettuce plant produced by the above methods, wherein the genetically modified lettuce plant comprises the genetic modification and otherwise comprises all of the physiological and morphological characteristics of lettuce cultivar ADEMPACK.

In still yet another aspect of the invention, the genetic complement of the lettuce cultivar ADEMPACK is provided. The phrase "genetic complement" is used to refer to the aggregate of nucleotide sequences, the expression of which sequences defines the phenotype of, in the present case, a lettuce plant, or a cell or tissue of that plant. A genetic complement thus represents the genetic makeup of a cell, tissue or plant, and a hybrid genetic complement represents the genetic makeup of a hybrid cell, tissue or plant. The invention thus provides lettuce plant cells that have a genetic complement in accordance with the lettuce plant cells disclosed herein, and plants, seeds and plants containing such cells. Plant genetic complements may be assessed by genetic marker profiles, and by the expression of phenotypic traits that are characteristic of the expression of the genetic complement, e.g., isozyme typing profiles.

In still yet another aspect, the invention provides a method of determining the genotype of a plant of lettuce cultivar ADEMPACK comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

This invention further relates to the $F_1$ hybrid lettuce plants and plant parts grown from the hybrid seed produced by crossing lettuce cultivar ADEMPACK to a second lettuce plant. Still further included in the invention are the seeds of an $F_1$ hybrid plant produced with the lettuce cultivar ADEMPACK as one parent, the second generation ($F_2$) hybrid lettuce plant grown from the seed of the $F_1$ hybrid plant, and the seeds of the $F_2$ hybrid plant. Thus, any such methods using the lettuce cultivar ADEMPACK are part of this invention: selfing, backcrosses, hybrid production, crosses to populations, and the like. All plants produced using lettuce cultivar ADEMPACK as at least one parent are within the scope of this invention. Advantageously, the lettuce cultivar could be used in crosses with other, different, lettuce plants to produce first generation ($F_1$) lettuce hybrid seeds and plants with superior characteristics.

The invention further provides methods for developing lettuce plants in a lettuce plant breeding program using plant breeding techniques including but not limited to recurrent selection, backcrossing, pedigree breeding, restriction fragment length polymorphism enhanced selection, genetic marker enhanced selection, and transformation. Seeds, lettuce plants, and parts thereof, produced by such breeding methods are also part of the invention.

This invention also relates to lettuce plants or breeding cultivars and plant parts derived from lettuce cultivar ADEMPACK. Still yet another aspect of the invention is a method of producing a lettuce plant derived from the lettuce cultivar ADEMPACK, the method comprising the steps of: (a) preparing a progeny plant derived from lettuce cultivar ADEMPACK by crossing a plant of the lettuce cultivar ADEMPACK with a second lettuce plant; and (b) crossing the progeny plant with itself or a second plant to produce a seed of a progeny plant of a subsequent generation which is derived from a plant of the lettuce cultivar ADEMPACK. In further embodiments of the invention, the method may additionally comprise: (c) growing a progeny plant of a subsequent generation from said seed of a progeny plant of a subsequent generation and crossing the progeny plant of a subsequent generation with itself or a second plant; and repeating the steps for an additional 2-10 generations to produce a lettuce plant derived from the lettuce cultivar ADEMPACK. The plant derived from lettuce cultivar ADEMPACK may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from lettuce cultivar ADEMPACK is obtained which possesses some of the desirable traits of the line as well as potentially other selected traits. Also provided by the invention is a plant produced by this and the other methods of the invention.

In another embodiment of the invention, the method of producing a lettuce plant derived from the lettuce cultivar ADEMPACK further comprises: (a) crossing the lettuce cultivar ADEMPACK-derived lettuce plant with itself or another lettuce plant to yield additional lettuce cultivar ADEMPACK-derived progeny lettuce seed; (b) growing the progeny lettuce seed of step (a) under plant growth conditions to yield additional lettuce cultivar ADEMPACK-derived lettuce plants; and (c) repeating the crossing and growing steps of (a) and (b) to generate further lettuce cultivar ADEMPACK-derived lettuce plants. In specific embodiments, steps (a) and (b) may be repeated at least 1, 2, 3, 4, or 5 or more times as desired. The invention still further provides a lettuce plant produced by this and the foregoing methods.

The invention also provides methods of multiplication or propagation of lettuce plants of the invention, which can be accomplished using any method known in the art, for example, via vegetative propagation and/or seed. Still further, as another aspect, the invention provides a method of vegetatively propagating a plant of lettuce cultivar ADEMPACK. In a non-limiting example, the method comprises: (a) collecting a plant part capable of being propagated from a plant of lettuce cultivar ADEMPACK; (b) producing at least a first rooted plant from said plant part. The invention also encompasses the plantlets and plants produced by these methods.

The invention further relates to a method of producing a commodity plant product from lettuce cultivar ADEMPACK, such as fresh lettuce leaf, fresh lettuce head, cut, sliced, ground, pureed, dried, canned, jarred, washed, packaged, frozen and/or heated leaves, and to the commodity plant product produced by the method.

In addition to the exemplary aspects and embodiments described above, further aspects and embodiments will become apparent by reference by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Allele. The allele is any of one or more alternative forms of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

Backcrossing. A process in which a breeder crosses progeny back to one of the parental genotypes one or more times. Commonly used to introduce one or more locus conversions from one genetic background into another (backcross conversion).

Bolting. The premature development of a flowering stalk, and subsequent seed, before a plant produces a food crop. Bolting is typically caused by late planting when temperatures are low enough to cause vernalization of the plants.

*Bremia lactucae.* An Oomycete that causes downy mildew in lettuce in cooler growing regions.

Cell. Cell as used herein includes a plant cell, whether isolated, in tissue culture or incorporated in a plant or plant part. The cell can be a cell, such as a somatic cell, of the variety having the same set of chromosomes as the cells of the deposited seed, or, if the cell contains a locus conversion or transgene, otherwise having the same or essentially the same set of chromosomes as the cells of the deposited seed.

Core diameter. The diameter of the lettuce stem at the base of the cut head.

Core length. Length of the internal lettuce stem measured from the base of the cut and trimmed head to the tip of the stem.

Corky root. A disease caused by the bacterium *Rhizomonas suberifaciens*, which causes the entire taproot to become brown, severely cracked, and non-functional.

Cotyledon. One of the first leaves of the embryo of a seed plant; typically one or more in monocotyledons, two in dicotyledons, and two or more in gymnosperms.

Essentially all of the physiological and morphological characteristics. A plant having essentially all of the physiological and morphological characteristics of a designated plant has all of the characteristics of the plant that are otherwise present when compared in the same environment, other than an occasional variant trait that might arise during backcrossing or direct introduction of a transgene.

$F_\#$. The "F" symbol denotes the filial generation, and the # is the generation number, such as $F_1$, $F_2$, $F_3$, etc.

$F_1$ Hybrid. The first generation progeny of the cross of two nonisogenic plants.

First water date. The date the seed first receives adequate moisture to germinate. This can and often does equal the planting date.

Frame diameter. The frame diameter is a measurement of the lettuce plant diameter at its widest point, measured from the outer most wrapper leaf tip to the outer most wrapper leaf tip.

*Fusarium oxysporum. Fusarium* wilt of lettuce is caused by the soil-borne fungus *Fusarium oxysporum* f. sp. *lactucae*. There are three reported races of *Fusarium oxysporum* f sp. *lactucae*. All three races are present in Japan, whereas only race 1 is known to occur in the United States (Arizona and California). Infection results in yellowing and necrosis of leaves, as well as stunted, wilted plants and often plant death.

Gene. As used herein, "gene" refers to a segment of nucleic acid. A gene can be introduced into a genome of a species, whether from a different species or from the same species, using transformation or various breeding methods.

Gene silencing. The interruption or suppression of the expression of a gene at the level of transcription or translation.

Genetically modified. Describes an organism that has received genetic material from another organism, or had its genetic material modified, resulting in a change in one or more of its phenotypic characteristics. Methods used to modify, introduce or delete the genetic material may include mutation breeding, genome editing, RNA interference, gene silencing, backcross conversion, genetic transformation, single and multiple gene conversion, and/or direct gene transfer.

Genome editing. A type of genetic engineering in which DNA is inserted, replaced, modified or removed from a genome using artificially engineered nucleases or other targeted changes using homologous recombination. Examples include but are not limited to use of zinc finger nucleases (ZFNs), TAL effector nucleases (TALENs), meganucleases, CRISPR/Cas9, and other CRISPR related technologies. (Ma et. al., *Molecular Plant*, 9:961-974 (2016); Belhaj et. al., *Current Opinion in Biotechnology*, 32:76-84 (2015)).

Genotype. Refers to the genetic constitution of a cell or organism.

Green leaf lettuce. A type of lettuce characterized by having curled or incised leaves forming a loose green rosette that does not develop into a compact head.

Haploid. A cell or organism having one set of the two sets of chromosomes in a diploid.

Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Iceberg lettuce. A type of lettuce characterized by having a large, firm head with a crisp texture and a white or creamy yellow interior.

*Impatiens* necrotic spot virus (INSV). A tospovirus transmitted by *thrips* which causes leaves of infected plants to develop brown to dark brown spots and dead (necrotic) areas, making heads of infected plants unmarketable. INSV has symptoms similar to tomato spotted wilt virus (TSWV).

Lettuce big vein virus (LBV). Big vein is a disease of lettuce caused by lettuce mirafiori big vein virus which is transmitted by the fungus Olpidium virulentus, with vein clearing and leaf shrinkage resulting in plants of poor quality and reduced marketable value.

Lettuce mosaic virus. A disease that can cause a stunted, deformed, or mottled pattern in young lettuce and yellow, twisted, and deformed leaves in older lettuce.

Lettuce necrotic stunt virus (LNSV). A disease of lettuce that can cause severely stunted plants having yellowed outer leaves and brown, necrotic spotting. LNSV is a soil-borne virus from the Tombusvirus family with no known vector.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A defined segment of DNA.

Locus conversion (also called a 'trait conversion' or 'gene conversion'). A locus conversion refers to a plant or plants within a variety or line that have been modified in a manner that retains the overall genetics of the variety and further comprises one or more loci with a specific desired trait, such as but not limited to male sterility, insect or pest control, disease control or herbicide tolerance. Examples of single locus conversions include mutant genes, transgenes and native traits finely mapped to a single locus. One or more locus conversion traits may be introduced into a single cultivar.

Market stage. Market stage is the stage when a lettuce plant is ready for commercial lettuce harvest.

Maturity date. Maturity refers to the stage when the plants are of full size or optimum weight, in marketable form or shape to be of commercial or economic value.

*Nasonovia ribisnigri*. A lettuce aphid that colonizes the innermost leaves of the lettuce plant, contaminating areas that cannot be treated easily with insecticides.

Pedigree. Refers to the lineage or genealogical descent of a plant.

Pedigree distance. Relationship among generations based on their ancestral links as evidenced in pedigrees. May be measured by the distance of the pedigree from a given starting point in the ancestry.

Plant. "Plant" includes plant cells, plant protoplasts, plant tissue, plant cells of tissue culture from which lettuce plants can be regenerated, plant calli, plant clumps and plant cells that are intact in plants, or parts of plants such as pollen, flowers, seeds, leaves, stems and the like.

Plant part. Includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

Quantitative Trait Loci. Quantitative Trait Loci (QTL) refers to genetic loci that control to some degree, numerically representable traits that are usually continuously distributed.

Ratio of head height/diameter. Head height divided by the head diameter is an indication of the head shape; <1 is flattened, 1=round, and >1 is pointed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Rogueing. Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Romaine lettuce. A lettuce variety having elongated upright leaves forming a loose, loaf-shaped head and the outer leaves are usually dark green.

*Sclerotinia sclerotiorum*. A plant pathogenic fungus that can cause a disease called white mold. Also known as cottony rot, watery soft rot, stem rot, drop, crown rot and blossom blight.

Single locus converted (conversion) plant. Plants which are developed by a plant breeding technique called backcrossing or via genetic engineering wherein essentially all of the morphological and physiological characteristics of a variety are recovered in addition to the desired trait or characteristics conferred by the single locus transferred into the variety via the backcrossing technique or via genetic engineering. A single locus may comprise one gene, or in the case of transgenic plants, one or more transgenes integrated into the host genome at a single site (locus).

Tipburn. Means a browning of the edges or tips of lettuce leaves that has an unknown cause, possibly a calcium deficiency.

Tomato bushy stunt virus (TBSV). A virus of the tombusvirus family that causes a disease known as lettuce dieback characterized by yellowing, necrosis, stunting, and death of lettuce plants.

Transgene. A nucleic acid of interest that can be introduced into the genome of a plant by genetic engineering techniques (e.g., transformation) or breeding.

The following detailed description is of the currently contemplated modes of carrying out the invention. The description is not to be taken in a limiting sense, but is made merely for the purpose of illustrating the general principles of the invention, since the scope of the invention is best defined by the appended claims.

Lettuce cultivar ADEMPACK is a novel romaine lettuce variety that has a medium head size with an elliptic shape, and white seed color. Lettuce cultivar ADEMPACK has resistance to tomato bushy stunt virus (TBSV) and downy mildew, and tolerance to *Fusarium* Oysporum *Lactucae* Race 1 and Lettuce Big Vein Virus (LB V). The romaine lettuce variety exemplified in the present invention, ADEMPACK, is different from known varieties of romaine lettuce in having an unexpected and unique combination of traits. Lettuce cultivar ADEMPACK is adapted to the spring, autumn, and winter growing region in the Yuma, Arizona area. Additionally, lettuce cultivar ADEMPACK is resistant to tipburn and is resistant to lettuce aphid (*Nasonovia ribisnigri*).

Lettuce cultivar ADEMPACK has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in cultivar ADEMPACK.

Lettuce cultivar ADEMPACK has the following morphological and physiological characteristics described (based on data collected in Yuma, Arizona):

TABLE 1

VARIETY DESCRIPTION INFORMATION

Plant:

Type: Romaine lettuce
Maturity date: Dec. 22, 2021
Seed:

Color: White
Light dormancy: No
Heat dormancy: No
Cotyledon (to fourth leaf stage):

Shape: Intermediate
Shape of fourth leaf: Elongated
Length/width index of $4^{th}$ leaf (L/W × 10): 12 (1.8/1 × 10 cm)
Apex: Rounded
Base: Broad
Undulation: Slight
Green color: Green
Anthocyanin distribution: None
Rolling: No
Cupping: Slight
Reflexing: Yes
Mature Leaves:
Margin:

Incision depth: Shallow
Indentation: No
Undulation of the apical margin: Medium
Green color (at harvest maturity): Green
Hue of green color of outer leaves: Glossy
Intensity of color of outer leaves: Medium
Anthocyanin distribution: None
Blistering: Medium
Glossiness: Medium
Thickness: Thick
Trichomes: None
Plant (at market stage):

Spread of frame leaves: 40.4 cm
Head diameter: 12.0 cm
Head shape: Elliptic
Head size class: Medium
Head weight: 690.0 g
Head firmness: Very Firm
Butt:

Shape: Rounded
Midrib: Semi raised
Core:

Diameter at base of head: 14.5 cm
Core height from base of head to apex: 3.2 cm
Bolting:

First water date: Dec. 8, 2021
Number of days from first water date to seed stalk emergence: 105
Time of beginning of bolting: Late
Class: Slow Bolting
Height of mature seed stalk: 92.8 cm
Spread of bolter plant: 36.5 cm
Bolter leaves: Broad
Bolter leaf margin: Crenate
Bolter leaf color: Green
Bolter habit:

Terminal inflorescence: Yes
Lateral shoots: Yes
Basal side shoots: No
Primary Regions of Adaptation:

Spring area: Yuma, Arizona
Summer area: Not adapted
Autumn area: Yuma, Arizona
Winter area: Yuma, Arizona

TABLE 1-continued

VARIETY DESCRIPTION INFORMATION

Disease/Pest Resistance:

Lettuce mosaic virus: No
Lettuce necrotic stunt virus (LNSV): No
Tomato bushy stunt virus (TBSV): Yes
Fusarium Oysporum Lactucae Race 1: Tolerant
Lettuce big vein virus: Tolerant
Downy mildew (*Bremia lactucae*): Yes (CA 1-9)
Physiological Responses:

Tipburn: Yes

Further Embodiments of the Invention

Lettuce in general, and romaine lettuce in particular, is an important and valuable vegetable crop. Thus, a continuing goal of lettuce plant breeders is to develop stable, high yielding lettuce cultivars that are agronomically sound. To accomplish this goal, the lettuce breeder must select and develop lettuce plants with traits that result in superior cultivars.

Plant breeding techniques known in the art and used in a lettuce plant breeding program include, but are not limited to, pedigree breeding, recurrent selection, mass selection, single or multiple-seed descent, bulk selection, backcrossing, open pollination breeding, restriction fragment length polymorphism enhanced selection, genetic marker enhanced selection, making double haploids, and transformation. Often combinations of these techniques are used. The development of lettuce varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Using Lettuce Cultivar ADEMPACK to Develop Other Lettuce Varieties

This invention is directed to methods for producing a lettuce plant by crossing a first parent lettuce plant with a second parent lettuce plant wherein either the first or second parent lettuce plant is variety ADEMPACK. Also provided are methods for producing a lettuce plant having substantially all of the morphological and physiological characteristics of cultivar ADEMPACK, by crossing a first parent lettuce plant with a second parent lettuce plant wherein the first and/or the second parent lettuce plant is a plant having substantially all of the morphological and physiological characteristics of cultivar ADEMPACK set forth in Table 1, as determined at the 5% significance level when grown in the same environmental conditions. The other parent may be any lettuce plant, such as a lettuce plant that is part of a synthetic or natural population. Any such methods using lettuce cultivar ADEMPACK include but are not limited to selfing, sibbing, backcrossing, mass selection, pedigree breeding, bulk selection, hybrid production, crossing to populations, and the like. These methods are well known in the art and some of the more commonly used breeding methods are described below. Descriptions of breeding methods can be found in one of several reference books (e.g., Allard, Principles of Plant Breeding, 1960; Simmonds, Principles of Crop Improvement, 1979; Fehr, "Breeding Methods for Cultivar Development", Chapter 7, Lettuce Improvement, Production and Uses, 2.sup.nd ed., Wilcox editor, 1987).

Another method involves producing a population of lettuce cultivar ADEMPACK progeny lettuce plants, comprising crossing variety ADEMPACK with another lettuce plant, thereby producing a population of lettuce plants which, on average, derive 50% of their alleles from lettuce cultivar ADEMPACK. A plant of this population may be selected and repeatedly selfed or sibbed with a lettuce cultivar resulting from these successive filial generations. One embodiment of this invention is the lettuce cultivar produced by this method and that has obtained at least 50% of its alleles from lettuce cultivar ADEMPACK.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus the invention includes lettuce cultivar ADEMPACK progeny lettuce plants comprising a combination of at least two of variety ADEMPACK traits selected from the group consisting of those listed in Table 1, or the variety ADEMPACK combination of traits listed in the Detailed Description of the Invention, so that said progeny lettuce plant is not significantly different for said traits than lettuce cultivar ADEMPACK as determined at the 5% significance level when grown in the same environmental conditions. Using techniques described herein, molecular markers may be used to identify said progeny plant as a lettuce cultivar ADEMPACK progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

The goal of lettuce plant breeding is to develop new, unique, and superior lettuce cultivars. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level and the cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. Therefore, two breeders will never develop the same line, or even very similar lines, having the same lettuce traits.

Progeny of lettuce cultivar ADEMPACK may also be characterized through their filial relationship with lettuce cultivar ADEMPACK, as for example, being within a certain number of breeding crosses of lettuce cultivar ADEMPACK. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce cultivar ADEMPACK and its progeny. For example, progeny produced by the methods described herein may be within 1, 2, 3, 4, or 5 breeding crosses of lettuce cultivar ADEMPACK.

Pedigree breeding starts with the crossing of two genotypes, such as lettuce cultivar ADEMPACK or a lettuce variety having all of the morphological and physiological characteristics of ADEMPACK, and another lettuce variety having one or more desirable characteristics that is lacking or which complements lettuce cultivar ADEMPACK. If the two original parents do not provide all the desired characteristics, other sources can be included in the breeding population. In the pedigree method, superior plants are selfed and selected in successive filial generations. In the succeeding filial generations, the heterozygous condition gives way to the homozygous allele condition as a result of inbreeding. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. In some examples, 1, 2, 3, 4, 5, 6, 7, 8, 9, 10, or more generations of selfing and selection are practiced. After a sufficient amount of inbreeding, successive filial generations will serve to increase seed of the developed variety. Preferably, the developed variety comprises homozygous alleles at about 95% or more of its loci.

In addition to being used to create backcross conversion populations, backcrossing can also be used in combination with pedigree breeding. As discussed previously, backcrossing can be used to transfer one or more specifically desirable traits from one variety (the donor parent) to a developed variety (the recurrent parent), which has good overall agronomic characteristics yet may lack one or more other desirable traits. However, the same procedure can be used to move the progeny toward the genotype of the recurrent parent but at the same time retain many components of the non-recurrent parent by stopping the backcrossing at an early stage and proceeding with selfing and selection. For example, a lettuce variety may be crossed with another variety to produce a first-generation progeny plant. The first-generation progeny plant may then be backcrossed to one of its parent varieties to create a BCiFi. Progeny are selfed and selected so that the newly developed variety has many of the attributes of the recurrent parent and yet several of the desired attributes of the donor parent. This approach leverages the value and strengths of both parents for use in new lettuce varieties.

Therefore, in some examples a method of making a backcross conversion of lettuce cultivar ADEMPACK, comprising the steps of crossing a plant of lettuce cultivar ADEMPACK or a lettuce variety having all of the morphological and physiological characteristics of ADEMPACK with a donor plant possessing a desired trait to introduce the desired trait, selecting an $F_1$ progeny plant containing the desired trait, and backcrossing the selected $F_1$ progeny plant to a plant of lettuce cultivar ADEMPACK are provided. This method may further comprise the step of obtaining a molecular marker profile of lettuce cultivar ADEMPACK and using the molecular marker profile to select for a progeny plant with the desired trait and the molecular marker profile of ADEMPACK. The molecular marker profile can comprise information from one or more markers. In one example the desired trait is a mutant gene or transgene present in the donor parent. In another example, the desired trait is a native trait in the donor parent.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

Mutation breeding is another method of introducing new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Cultivar Development," Macmillan Publishing Company (1993). In addition, mutations created in other lettuce plants may be used to produce a backcross conversion of lettuce cultivar ADEMPACK that comprises such mutation.

Selection of lettuce plants for breeding is not necessarily dependent on the phenotype of a plant and instead can be based on genetic investigations. For example, one may utilize a suitable genetic marker which is closely associated with a trait of interest. One of these markers may therefore be used to identify the presence or absence of a trait in the offspring of a particular cross, and hence may be used in selection of progeny for continued breeding. This technique may commonly be referred to as marker assisted selection. Any other type of genetic marker or other assay which is able to identify the relative presence or absence of a trait of interest in a plant may also be useful for breeding purposes. Procedures for marker assisted selection applicable to the breeding of lettuces are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Isozyme Electrophoresis, Restriction Fragment Length Polymorphisms (RFLPs), Simple Sequence Length Polymorphisms (SSLPs) (Williams et al., Nucleic Acids Res., 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), Simple Sequence Repeats (SSRs), and Single Nucleotide Polymorphisms (SNPs) (Wang et al., Science, 280:1077-1082, 1998).

The production of double haploids can also be used for the development of homozygous varieties in a breeding program. Double haploids are produced by the doubling of a set of chromosomes from a heterozygous plant to produce a completely homozygous individual. For example, see, Wan, et al., "Efficient Production of Doubled Haploid Plants Through Colchicine Treatment of Anther-Derived Maize Callus," Theoretical and Applied Genetics, 77:889-892 (1989) and U.S. Pat. No. 7,135,615. This can be advantageous because the process omits the generations of selfing needed to obtain a homozygous plant from a heterozygous source.

Descriptions of other breeding methods that are commonly used for different traits and crops can be found in one of several reference books (e.g., Allard, "Principles of plant breeding," John Wiley & Sons, NY, University of California, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: Soybeans: Improvement, Production and Uses," 2d Ed., Manograph 16:249, 1987; Fehr, "Principles of cultivar development," Theory and Technique (Vol 1) and Crop Species Soybean (Vol 2), Iowa State Univ., Macmillian Pub. Co., NY, 360-376, 1987; Poehlman and Sleper, "Breeding Field Crops" Iowa State University Press, Ames, 1995; Sprague and Dudley, eds., Corn and Improvement, 5th ed., 2006).

Genotypic Profile of ADEMPACK and Progeny

In addition to phenotypic observations, a plant can also be identified by its genotype. The genotype of a plant can be characterized through a genetic marker profile which can identify plants of the same variety or a related variety, or which can be used to determine or validate a pedigree. Genetic marker profiles can be obtained by techniques such as restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) also referred to as microsatellites, single nucleotide polymorphisms (SNPs), or genome-wide evaluations such as genotyping-by-sequencing (GB S). For example, see Cregan et al. (1999) "An Integrated Genetic Linkage Map of the Soybean Genome" Crop Science 39:1464-1490, and Berry et al. (2003) "Assessing Probability of Ancestry Using Simple Sequence Repeat Profiles: Applications to Maize Inbred Lines and Soybean Varieties" Genetics 165:331-342, each of which are incorporated by reference herein in their entirety. Favorable genotypes and or marker profiles, optionally associated with a trait of interest, may be identified by one or more methodologies.

In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) *PLoS ONE* 6:e19379), and expression methods. In some examples, no reference genome sequence is needed in order to complete the analysis.

The invention further provides a method of determining the genotype of a plant of lettuce cultivar ADEMPACK, or a first-generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of lettuce cultivar ADEMPACK.

With any of the genotyping techniques mentioned herein, polymorphisms may be detected when the genotype and/or sequence of the plant of interest is compared to the genotype and/or sequence of one or more reference plants. The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers. The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

In some examples, a plant, a plant part, or a seed of lettuce cultivar ADEMPACK may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like.

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Particular markers used for these purposes are not limited to the set of markers disclosed herein, but may include any type of marker and marker profile which provides a means of distinguishing varieties. In addition to being used for identification of lettuce cultivar ADEMPACK, a hybrid produced through the use of ADEMPACK, and the identification or verification of pedigree for progeny plants produced through the use of ADEMPACK, a genetic marker profile is also useful in developing a locus conversion of ADEMPACK.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

The SSR profile of lettuce cultivar ADEMPACK can be used to identify plants comprising lettuce cultivar ADEMPACK as a parent, since such plants will comprise the same homozygous alleles as lettuce cultivar ADEMPACK. Because the lettuce variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of lettuce cultivar ADEMPACK in their development, such as lettuce cultivar ADEMPACK comprising a locus conversion, backcross conversion, transgene, or genetic sterility factor, may be identified by having a molecular marker profile with a high percent identity to lettuce cultivar ADEMPACK. Such a percent identity might be 95%, 96%, 97%, 98%, 99%, 99.5%, or 99.9% identical to lettuce cultivar ADEMPACK.

The SSR profile of lettuce cultivar ADEMPACK can also be used to identify essentially derived varieties and other progeny varieties developed from the use of lettuce cultivar ADEMPACK, as well as cells and other plant parts thereof. Such plants may be developed using the markers identified in WO 00/31964, U.S. Pat. Nos. 6,162,967, and 7,288,386. Progeny plants and plant parts produced using lettuce cultivar ADEMPACK may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from lettuce cultivar ADEMPACK, as measured by either percent identity or percent similarity. Such progeny may be further characterized as being within a pedigree distance of lettuce cultivar ADEMPACK, such as within 1, 2, 3, 4, or 5 or less cross-pollinations to a lettuce plant other than lettuce cultivar ADEMPACK or a plant that has lettuce cultivar ADEMPACK as a progenitor. Unique molecular profiles may be identified with other molecular tools such as SNPs and RFLPs.

While determining the genotypic profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Molecular data from ADEMPACK may be used in a plant breeding process. Nucleic acids may be isolated from a seed of ADEMPACK or from a plant, plant part, or cell produced by growing a seed of ADEMPACK, or from a seed of ADEMPACK with a locus conversion, or from a plant, plant part, or cell of ADEMPACK with a locus conversion. One or more polymorphisms may be isolated from the nucleic acids. A plant having one or more of the identified polymorphisms may be selected and used in a plant breeding method to produce another plant.

Introduction of a New Trait or Locus into Lettuce Cultivar ADEMPACK

Cultivar ADEMPACK represents a new base genetic variety into which a new locus or trait may be introgressed. Backcrossing and direct transformation represent two important methods that can be used to accomplish such an introgression.

Single Locus Conversions

When the term "lettuce plant" is used in the context of the present invention, this also includes any single locus conversions of that variety. The term "single locus converted plant" or "single gene converted plant" refers to those lettuce plants which are developed by backcrossing or genetic engineering, wherein essentially all of the desired morphological and physiological characteristics of a variety are recovered in addition to the one or more genes transferred into the variety via the backcrossing technique or genetic engineering. Backcrossing methods can be used with the present invention to improve or introduce a characteristic into the variety.

A backcross conversion of lettuce cultivar ADEMPACK occurs when DNA sequences are introduced through backcrossing (Hallauer, et al., "Corn Breeding," *Corn and Corn Improvements*, No. 18, pp. 463-481 (1988)), with lettuce cultivar ADEMPACK utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, *Proceedings Symposium of the Analysis of Molecular Data*, Crop Science Society of America, Corvallis, Oregon (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. In addition, an introgression site itself, such as an FRT site, Lox site, or other site-specific integration site, may be inserted by backcrossing and utilized for direct insertion of one or more genes of interest into a specific plant variety.

A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site-specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in lettuce cultivar ADEMPACK comprises crossing lettuce cultivar ADEMPACK plants grown from lettuce cultivar ADEMPACK seed with plants of another lettuce variety that comprise the desired trait or locus, selecting $F_1$ progeny plants that comprise the desired trait or locus to produce selected $F_1$ progeny plants, crossing the selected progeny plants with the lettuce cultivar ADEMPACK plants to produce backcross progeny plants, selecting for backcross progeny plants that have the desired trait or locus and the morphological characteristics of lettuce cultivar ADEMPACK to produce selected backcross progeny plants, and backcrossing to lettuce cultivar ADEMPACK three or more times in succession to produce selected fourth or higher backcross progeny plants that comprise said trait or locus. The modified lettuce cultivar ADEMPACK may be further characterized as having the physiological and morphological characteristics of lettuce cultivar ADEMPACK listed in Table 1 as determined at the 5% significance level when grown in the same environmental conditions and/or may be characterized by percent similarity or identity to lettuce cultivar ADEMPACK as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny lettuce seed by adding a step at the end of the process that comprises crossing lettuce cultivar ADEMPACK with the introgressed trait or locus with a different lettuce plant and harvesting the resultant first generation progeny lettuce seed.

Methods for Genetic Engineering of Lettuce

With the advent of molecular biological techniques that have allowed the isolation and characterization of genes that encode specific protein products, scientists in the field of plant biology developed a strong interest in engineering the genome of plants (genetic engineering) to contain and express foreign genes, or additional, or modified versions of native, or endogenous, genes (perhaps driven by different promoters) in order to alter the traits of a plant in a specific manner. Plants altered by genetic engineering are often referred to as 'genetically modified'. Any DNA sequences, whether from a different species or from the same species, which are introduced into the genome using transformation and/or various breeding methods, are referred to herein collectively as "transgenes." Over the last fifteen to twenty years, several methods for producing transgenic plants have been developed, and the present invention, in particular embodiments, also relates to transformed versions of the claimed cultivar.

Vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus. A vector can be introduced into lettuce cells by known methods, such as the polyethylene glycol method, polycation method, electroporation, *Agrobacterium*-mediated transfer, particle bombardment and direct DNA uptake by protoplasts. See, e.g., Pang et al. (The Plant J., 9, 899-909, 1996).

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson (Eds.), CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson (Eds.), CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., Science, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for *Agrobacterium*-mediated gene transfer are provided by Gruber, et al., supra, Miki, et al., supra, and Moloney, et al., Plant Cell Rep., 8:238 (1989). See also, U.S. Pat. No. 5,563,055 (Townsend and Thomas), issued Oct. 8, 1996.

*Agrobacterium*-mediated transfer is a widely applicable system for introducing gene loci into plant cells, including lettuce. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., Bio. Tech., 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio. Tech.*, 3(7):629-635, 1985; U.S. Pat. No. 5,563,055). For example, U.S. Pat. No. 5,349,124 describes a method of transforming lettuce plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in lettuce having resistance to such insects.

B. Direct Gene Transfer:

Several methods of plant transformation, collectively referred to as direct gene transfer, have been developed as an alternative to *Agrobacterium*-mediated transformation. A generally applicable method for delivering transforming DNA segments to plant cells is microprojectile-mediated transformation, or microprojectile bombardment. In this method, particles are coated with nucleic acids and delivered into cells by a propelling force. Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol Plant*, 7:206 (1990); Klein, et al., *Bio/Technology*, 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985); Christou, et al., *PNAS*, 84:3962 (1987). Direct uptake of DNA into protoplasts using $CaCl_2$) precipitation, calcium phosphate precipitation, polyethylene glycol treatment, polyvinyl alcohol, or poly-L-ornithine has also been reported. See, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988; Hain, et al., *Mol. Gen. Genet.*, 199:161, 1985 and Draper, et al., *Plant Cell Physiol.* 23:451, 1982.

Electroporation of protoplasts and whole cells and tissues has also been described. Donn, et al., In Abstracts of VIIth International Congress on Plant Cell and Tissue Culture IAPTC, A2-38, p. 53, 1990; D'Halluin, et al., *Plant Cell*, 4:1495-1505, 1992; and Spencer, et al., *Plant Mol. Biol.*, 24:51-61, 1994. Another illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target lettuce cells.

Transformation of plants and expression of foreign genetic elements is exemplified in Choi et al., *Plant Cell Rep.*, 13: 344-348, 1994 and Ellul et al., *Theor. Appl. Genet.*, 107:462-469, 2003.

Following transformation of lettuce target tissues, expression of selectable marker genes allows for preferential selection of transformed cells, tissues, and/or plants, using regeneration and selection methods now well known in the art.

The methods described herein for transformation would typically be used for producing a transgenic variety. The transgenic variety could then be crossed, with another (non-transformed or transformed) variety, in order to produce a new transgenic variety. Alternatively, a genetic trait which has been engineered into a particular lettuce cultivar using the transformation techniques described could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Expression Vectors for Lettuce Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., *Plant Mol. Biol.*, 5:387 (1987); Teeri, et al., *EMBO J.*, 8:343 (1989); Koncz, et al., *PNAS*, 84:131 (1987); and DeBlock, et al., *EMBO J.*, 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for Lettuce Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in lettuce. Optionally, the inducible promoter is operably linked to a nucleotide sequence encoding a signal sequence which is operably linked to a gene for expression in lettuce. With an inducible promoter, the rate of transcription increases in response to an inducing agent.

Any inducible promoter can be used in the instant invention. See Ward, et al., *Plant Mol. Biol.*, 22:361-366 (1993). Exemplary inducible promoters include, but are not limited to, that from the ACEI system which responds to copper (Meft, et al., *PNAS*, 90:4567-4571 (1993)); In2 gene from maize which responds to benzenesulfonamide herbicide safeners (Hershey, et al., *Mol. Gen. Genet.*, 227:229-237 (1991) and Gatz, et al., *Mol. Gen. Genet.*, 243:32-38 (1994)) or Tet repressor from Tn10 (Gatz, et al., *Mol. Gen. Genet.*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS*, 88:0421 (1991).

B. Constitutive Promoters:

A constitutive promoter is operably linked to a gene for expression in lettuce or the constitutive promoter is operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J., 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Additional Methods for Genetic Engineering of Lettuce

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system and other similar methods. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1, incorporated herein by reference).

A genetic map can be generated that identifies the approximate chromosomal location of an integrated DNA molecule, for example via conventional restriction fragment length polymorphisms (RFLP), polymerase chain reaction (PCR) analysis, simple sequence repeats (SSR), and single nucleotide polymorphisms (SNP). For exemplary methodologies in this regard, see Glick and Thompson, Methods in Plant Molecular Biology and Biotechnology, pp. 269-284 (CRC Press, Boca Raton, 1993).

Wang et al. discuss "Large Scale Identification, Mapping and Genotyping of Single-Nucleotide Polymorphisms in the Human Genome", Science (1998) 280:1077-1082, and similar capabilities are increasingly available for the lettuce genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons could involve hybridizations, RFLP, PCR, SSR, sequencing or combinations thereof, all of which are conventional techniques. SNPs may also be used alone or in combination with other techniques.

Lettuce Cultivar ADEMPACK Further Comprising a Transgene

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. One or more transgenes of interest can be introduced into lettuce cultivar ADEMPACK. Transgenic variants of lettuce cultivar ADEMPACK plants, seeds, cells, and parts thereof or derived therefrom are provided. Transgenic variants of ADEMPACK comprise the physiological and morphological characteristics of lettuce cultivar ADEMPACK, such as listed in Table 1 as determined at the 5% significance level when grown in the same environmental conditions, and/or may be characterized or identified by percent similarity or identity to ADEMPACK as determined by SSR or other molecular markers. In some examples, transgenic variants of lettuce cultivar ADEMPACK are produced by introducing at least one transgene of interest into lettuce cultivar ADEMPACK by transforming ADEMPACK with a polynucleotide comprising the transgene of interest. In other examples, transgenic variants of lettuce cultivar ADEMPACK are produced by introducing at least one transgene by introgressing the transgene into lettuce cultivar ADEMPACK by crossing.

In one example, a process for modifying lettuce cultivar ADEMPACK with the addition of a desired trait, said process comprising transforming a lettuce plant of cultivar ADEMPACK with a transgene that confers a desired trait is provided. Therefore, transgenic ADEMPACK lettuce cells, plants, plant parts, and seeds produced from this process are provided. In some examples one more desired traits may include traits such as sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. The specific gene may be any known in the art or listed herein, including but not limited to a polynucleotide conferring resistance to an ALS-inhibitor herbicide, imidazolinone, sulfonylurea, protoporphyrinogen oxidase (PPO) inhibitors, hydroxyphenyl pyruvate dioxygenase (HPPD) inhibitors, glyphosate, glufosinate, triazine, 2,4-dichlorophenoxyacetic acid (2,4-D), dicamba, broxynil, metribuzin, or benzonitrile herbicides; a polynucleotide encoding a *Bacillus thuringiensis* polypeptide, a polynucleotide encoding a phytase, a fatty acid desaturase (e.g., FAD-2, FAD-3), galactinol synthase, a raffinose synthetic enzyme; or a polynucleotide conferring resistance to tipburn, *Bremia lactucae*, corky root, *Fusarium oxysporum*, lettuce big vein virus, lettuce mosaic virus, lettuce necrotic stunt virus, *Nasonovia ribisnigri*, *Sclerotinia sclerotiorum* or other plant pathogens.

Foreign Protein Genes and Agronomic Genes

By means of the present invention, plants can be genetically engineered to express various phenotypes of agronomic interest. Through the transformation of lettuce, the expression of genes can be altered to enhance disease resistance, insect resistance, herbicide resistance, agronomic, nutritional quality, and other traits. Transformation can also be used to insert DNA sequences which control or help control male-sterility. DNA sequences native to lettuce, as well as non-native DNA sequences, can be transformed into lettuce and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy, et al., *PNAS USA*, 85:8805-8809 (1988); and U.S. Pat. Nos. 5,107,065, 5,453,566, and 5,759,829); co-suppression (e.g., Taylor, Plant Cell, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334: 585-591 (1988)); hairpin structures (Smith, et al., *Nature*, 407:319-320 (2000); WO 99/53050; WO 98/53083); MicroRNA (Aukerman & Sakai, Plant Cell, 15:2730-2741 (2003)); ribozymes (Steinecke, et al., *EMBO J.*, 11:1525 (1992); Perriman, et al., *Antisense Res. Dev.*, 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary nucleotide sequences and/or native loci that confer at least one trait of interest, which optionally may be conferred or altered by genetic engineering, transformation or introgression of a transformed event include, but are not limited to, those categorized below:

A. Genes that Confer Resistance to Pests or Disease and that Encode:
1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., *Science*, 266:789 (1994) (cloning of the tomato Cf-9 gene for resistance to *Cladosporium fulvum*); Martin, et al., *Science*, 262:1432 (1993) (tomato Pto gene for resistance to *Pseudomonas syringae* pv. tomato encodes a protein kinase); and Mindrinos, et al., *Cell*, 78:1089 (1994) (*Arabidopsis* RSP2 gene for resistance to *Pseudomonas syringae*).
2. A *Bacillus thuringiensis* protein, a derivative thereof, or a synthetic polypeptide modeled thereon. Non-limiting examples of Bt transgenes being genetically engineered are given in the following patents and patent applications, and hereby are incorporated by reference for this purpose: U.S. Pat. Nos. 5,188,960; 5,689,052; 5,880,275; 5,986,177; 7,105,332; 7,208,474; WO91/14778; WO99/31248; WO01/12731; WO99/24581; WO97/40162; US2002/0151709; US2003/0177528; US2005/0138685; US/20070245427; US2007/0245428; US2006/0241042; US2008/0020966; US2008/0020968; US2008/0020967; US2008/0172762; US2008/0172762; and US2009/0005306.
3. A lectin. See, for example, the disclosure by Van Damme, et al., *Plant Mol. Biol.*, 24:25 (1994), who disclose the nucleotide sequences of several *Clivia miniata* mannose-binding lectin genes.
4. A vitamin-binding protein such as avidin. See PCT Application No. US 93/06487, the contents of which are hereby incorporated by reference. The application teaches the use of avidin and avidin homologues as larvicides against insect pests.
5. An enzyme inhibitor, for example, a protease or proteinase inhibitor, or an amylase inhibitor. See, for example, Abe, et al., *J Biol. Chem.*, 262:16793 (1987) (nucleotide sequence of rice cysteine proteinase inhibitor); Huub, et al., *Plant Mol. Biol.*, 21:985 (1993) (nucleotide sequence of cDNA encoding tobacco proteinase inhibitor I); and Sumitani, et al., *Biosci. Biotech. Biochem.*, 57:1243 (1993) (nucleotide sequence of *Streptomyces nitrosporeus* α-amylase inhibitor); and U.S. Pat. No. 5,494,813 (Hepher and Atkinson, issued Feb. 27, 1996).
6. An insect-specific hormone or pheromone, such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.
7. An insect-specific peptide or neuropeptide which, upon expression, disrupts the physiology of the affected pest. For example, see the disclosures of Regan, *J Biol. Chem.*, 269:9 (1994) (expression cloning yields DNA coding for insect diuretic hormone receptor); Pratt, et al., *Biochem. Biophys. Res. Comm.*, 163:1243 (1989) (an allostatin is identified in *Diploptera puntata*); Chattopadhyay, et al., *Critical Reviews in Microbiology*, 30(1):33-54 (2004); Zjawiony, *J Nat Prod,* 67(2):300-310 (2004); Carlini & Grossi-de-Sa, *Toxicon,* 40(11): 1515-1539 (2002); Ussuf, et al., *Curr Sci.,* 80(7):847-853 (2001); Vasconcelos & Oliveira, *Toxicon,* 44(4): 385-403 (2004). See also, U.S. Pat. No. 5,266,317 to Tomalski, et al., which discloses genes encoding insect-specific, paralytic neurotoxins.

8. An insect-specific venom produced in nature, by a snake, a wasp, etc. For example, see Pang, et al., *Gene,* 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Mol. Biol.,* 23:691 (1993), who teach the nucleotide sequence of a cDNA encoding tobacco hornworm chitinase, and Kawalleck, et al., *Plant Mol. Biol.,* 21:673 (1993), who provide the nucleotide sequence of the parsley ubi4-2 polyubiquitin gene.

11. A molecule that stimulates signal transduction. For example, see the disclosure by Botella, et al., *Plant Mol. Biol.,* 24:757 (1994), of nucleotide sequences for mung bean calmodulin cDNA clones, and Griess, et al., *Plant Physiol.,* 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., *Plant Sci.,* 89:43 (1993), of heterologous expression of a cecropin-β, lytic peptide analog to render transgenic tobacco plants resistant to *Pseudomonas solanacearum.*

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., *Ann. Rev. Phytopathol.,* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific or pathogen protein specific antibody. See, for example, Safarnej ad, et al. (2011) Biotechnology Advances 29(6): 961-971, reviewing antibody-mediated resistance against plant pathogens.

17. A developmental-arrestive protein produced in nature by a pathogen or a parasite. Thus, fungal endo-α-1, 4-D-polygalacturonases facilitate fungal colonization and plant nutrient released by solubilizing plant cell wall homo-α-1,4-D-galacturonase. See Lamb, et al., *Bio/technology,* 10:1436 (1992). The cloning and characterization of a gene which encodes a bean endopolygalacturonase-inhibiting protein is described by Toubart, et al., *Plant J.,* 2:367 (1992).

18. A developmental-arrestive protein produced in nature by a plant. For example, Logemann, et al., *Bio/technology,* 10:305 (1992), have shown that transgenic plants expressing the barley ribosome-inactivating gene have an increased resistance to fungal disease.

19. Genes involved in the Systemic Acquired Resistance (SAR) Response and/or the pathogenesis-related genes. See Fu et al. (2013) *Annu Rev Plant Biol.* 64:839-863, Luna et al. (2012) Plant Physiol. 158:844-853, Pieterse & Van Loon (2004) Curr Opin Plant Bio 7:456-64; and Somssich (2003) Cell 113:815-816.

20. Antifungal genes. See, Ceasar et al. (2012) Biotechnol Lett 34:995-1002; Bushnell et al. (1998) Can J Plant Path 20:137-149. Also, see US Patent Application Publications US2002/0166141; US2007/0274972; US2007/0192899; US2008/0022426; and U.S. Pat. Nos. 6,891,085; 7,306,946; and 7,598,346.

21. Detoxification genes, such as for fumonisin, beauvericin, moniliformin, and zearalenone and their structurally-related derivatives. For example, see Schweiger et al. (2013) Mol Plant Microbe Interact. 26:781-792 and U.S. Pat. Nos. 5,716,820; 5,792,931; 5,798,255; 5,846, 812; 6,083,736; 6,538,177; 6,388,171; and 6,812,380.

22. Cystatin and cysteine proteinase inhibitors. See, for example, Popovic et al. (2013) Phytochemistry 94:53-59. van der Linde et al. (2012) Plant Cell 24:1285-1300 and U.S. Pat. No. 7,205,453.

23. Defensin genes. See, for example, De Coninck et al. (2013) Fungal Biology Reviews 26: 109-120, International Patent Publication WO03/000863 and U.S. Pat. Nos. 6,911,577; 6,855,865; 6,777,592; and 7,238,781.

24. A lettuce mosaic potyvirus (LMV) coat protein gene introduced into *Lactuca sativa* in order to increase its resistance to LMV infection. See Dinant, et al., *Mol. Breeding,* 3:1, 75-86 (1997).

Any of the above listed disease or pest resistance genes (1-24) can be introduced into the claimed lettuce cultivar through a variety of means including but not limited to transformation and crossing.

B. Genes that Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., *EMBO J.,* 7:1241 (1988) and Miki, et al., *Theor.*

*Appl. Genet.,* 80:449 (1990), respectively. See also, U.S. Pat. Nos. 5,084,082; 5,605,011; 5,013,659; 5,141,870; 5,767,361; 5,731,180; 5,304,732; 4,761,373; 5,331,107; 5,928,937; and 5,378,824; US2007/0214515; US2013/0254944; and WO96/33270.

2. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. In addition, glyphosate resistance can be imparted to plants by the over expression of genes encoding glyphosate N-acetyltransferase. See, for example, US2004/0082770; US2005/0246798; and US2008/0234130 which are incorporated herein by reference for this purpose. A DNA molecule encoding a mutant aroA gene can be obtained under ATCC Accession No. 39256, and the nucleotide sequence of the mutant gene is disclosed in U.S. Pat. No. 4,769,061 to Comai. See also, Umaballava-Mobapathie in *Transgenic Research,* 8:1, 33-44 (1999) that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides, such as L-phosphinothricin. The nucleotide sequence of a phosphinothricin-acetyl-transferase gene is provided in European Application No. 0 242 246 to Leemans, et al. DeGreef, et al., *Bio/technology,* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc1-S3 genes described by Marshall, et al., *Theor. Appl. Genet.,* 83:435 (1992). For other polynucleotides and/or methods or uses see also U.S. Pat. Nos. 6,566,587; 6,338,961; 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; 7,608,761; 7,632,985; 8,053,184; 6,376,754; 7,407,913; and 5,491,288; EP1173580; WO01/66704; EP1173581; US2012/0070839; US2005/0223425; US2007/0197947; US2010/0100980; US2011/0067134; and EP1173582, which are incorporated herein by reference for this purpose.

3. An herbicide that inhibits photosynthesis, such as a triazine (psbA and gs+ genes) and a benzonitrile (nitrilase gene). Przibilla, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem.* 1, 285:173 (1992). The herbicide methyl viologen inhibits $CO_2$ assimilation. Foyer et al. (*Plant Physiol.,* 109:1047-1057, 1995) describe a plant overexpressing glutathione reductase (GR) which is resistant to methyl viologen treatment.

4. Acetohydroxy acid synthase, which has been found to make plants that express this enzyme resistant to multiple types of herbicides, has been introduced into a variety of plants. See Hattori, et al., *Mol. Gen. Genet.,* 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.,* 106:17 (1994)), genes for glutathione reductase and superoxide dismutase (Aono, et al., *Plant Cell Physiol.,* 36:1687 (1995)), and genes for various phosphotransferases (Datta, et al., *Plant Mol. Biol.,* 20:619 (1992)).

5. Protoporphyrinogen oxidase (PPO; protox) is the target of the PPO-inhibitor class of herbicides; a PPO-inhibitor resistant PPO gene was recently identified in *Amaranthus tuberculatus* (Patzoldt et al., *PNAS,* 103(33): 12329-2334, 2006). PPO is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

6. Genes that confer resistance to auxin or synthetic auxin herbicides. For example an aryloxyalkanoate dioxygenase (AAD) gene may confer resistance to arlyoxyalkanoate herbicides, such as 2,4-D, as well as pyridyloxyacetate herbicides, such as described in U.S. Pat. No. 8,283,522, and US2013/0035233. In other examples, a dicamba monooxygenase (DMO) is used to confer resistance to dicamba. Other polynucleotides of interest related to auxin herbicides and/or uses thereof include, for example, the descriptions found in U.S. Pat. Nos. 8,119,380; 7,812,224; 7,884,262; 7,855,326; 7,939,721; 7,105,724; 7,022,896; 8,207,092; US2011/067134; and US2010/0279866. Any of the above listed herbicide genes (1-6) can be introduced into the claimed lettuce cultivar through a variety of means including, but not limited to, transformation and crossing.

C. Genes that Confer or Contribute to a Value-Added Trait, Such as:

1. Increased iron content of the lettuce, for example, by introducing into a plant a soybean ferritin gene as described in Goto, et al., *Acta Horticulturae.,* 521, 101-109 (2000).
2. Decreased nitrate content of leaves, for example, by introducing into a lettuce a gene coding for a nitrate reductase. See, for example, Curtis, et al., *Plant Cell Rep.,* 18:11, 889-896 (1999).
3. Increased sweetness of the lettuce by introducing a gene coding for monellin that elicits a flavor 100,000 times sweeter than sugar on a molar basis. See Penarrubia, et al., *Bio/technology,* 10:561-564 (1992).
4. Modified fatty acid metabolism, for example, by introducing into a plant an antisense gene of stearyl-ACP desaturase to increase stearic acid content of the plant. See Knultzon, et al., *PNAS,* 89:2625 (1992).
5. Modified carbohydrate composition effected, for example, by introducing into plants a gene coding for an enzyme that alters the branching pattern of starch. See Shiroza, et al., *J. Bacteriol.*, 170:810 (1988) (nucleotide sequence of *Streptococcus* mutants fructosyltransferase gene); Steinmetz, et al., *Mol. Gen. Genet.*, 20:220 (1985) (nucleotide sequence of *Bacillus subtilis* levansucrase gene); Pen, et al., *Bio/technology*, 10:292 (1992) (production of transgenic plants that express *Bacillus lichenifonnis* α-amylase); Elliot, et al., *Plant Mol. Biol.*, 21:515 (1993) (nucleotide sequences of tomato invertase genes); Søgaard, et al., *J. Biol. Chem.*, 268:22480 (1993) (site-directed mutagenesis of barley α-amylase gene); and Fisher, et al., *Plant Physiol.*, 102:1045 (1993) (maize endosperm starch branching enzyme II).

6. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

D. Genes that Control Male-Sterility:
1. Introduction of a deacetylase gene under the control of a tapetum-specific promoter and with the application of the chemical N—Ac-PPT. See International Publication WO 01/29237.
2. Introduction of various stamen-specific promoters. See International Publications WO 92/13956 and WO 92/13957.
3. Introduction of the barnase and the barstar genes. See Paul, et al., *Plant Mol. Biol.*, 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640, all of which are hereby incorporated by reference.

E. Genes that Affect Abiotic Stress Resistance:
Genes that affect abiotic stress resistance (including but not limited to flowering, seed development, enhancement of nitrogen utilization efficiency, altered nitrogen responsiveness, drought resistance or tolerance, cold resistance or tolerance, high or low light intensity, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Tissue Culture

Further reproduction of the variety can occur by tissue culture and regeneration. Tissue culture of various tissues of lettuce and regeneration of plants therefrom is well known and widely published. For example, reference may be had to Teng, et al., *HortScience*, 27:9, 1030-1032 (1992); Teng, et al., *HortScience*, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., *Journal for the American Society for Horticultural Science*, 125:6, 669-672 (2000); and Ibrahim, et al., *Plant Cell Tissue and Organ Culture*, 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of variety ADEMPACK.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Table

Table 2 shows the results of a trial evaluation comparing the characteristics of lettuce cultivar ADEMPACK to similar romaine lettuce variety Green Towers, Sunbelt, and Del Sol. Table 2, column 1 shows the variety, column 2 shows the core diameter in centimeters, column 3 shows the head weight in grams, column 4 shows the head height centimeters, and column 5 shows the core length in centimeters of the four varieties.

TABLE 2

| Variety | Core Diameter (cm) | Head Weight (g) | Head Height (cm) | Core Length (cm) |
| --- | --- | --- | --- | --- |
| Adempack | 3.2 | 690 | 27.6 | 6.3 |
| Green Towers | 3.8 | 700 | 32.9 | 8.3 |

TABLE 2-continued

| Variety | Core Diameter (cm) | Head Weight (g) | Head Height (cm) | Core Length (cm) |
|---|---|---|---|---|
| Sunbelt | 3.6 | 684 | 30.4 | 7.9 |
| Del Sol | 3.7 | 689 | 30.8 | 8.1 |

As shown in Table 2, lettuce cultivar ADEMPACK is shorter in core diameter and core length than Green Towers, Sunbelt, and Del Sol. ADEMPACK holds similar head weight as that of the larger varieties in the comparison.

The present invention further provides a method of producing lettuce comprising a plant of lettuce cultivar ADEMPACK, wherein the plant has been cultivated to maturity, and collecting the lettuce from the plant.

As used herein, the term "plant" includes plant cells, plant protoplasts, plant cell tissue cultures from which lettuce plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Deposit Information

A deposit of the Southwest Genetics, LLC proprietary lettuce cultivar ADEMPACK disclosed above and recited in the appended claims has been made with the American Type Culture Collection (ATCC), 10801 University Boulevard, Manassas, Virginia 20110 under the terms of the Budapest Treaty. The date of deposit was Dec. 13, 2022. The deposit of 625 seeds was taken from the same deposit maintained by Southwest Genetics, LLC since prior to the filing date of this application. All restrictions will be irrevocably removed upon granting of a patent, and the deposit is intended to meet all requirements of 37 C.F.R. §§ 1.801-1.809. The ATCC Accession Number is PTA-127481. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A plant, plant part, or seed of lettuce cultivar ADEMPACK, wherein a representative sample of seed of said cultivar was deposited under ATCC Accession No. PTA-127481.

2. The plant part of claim 1, further defined as pollen, a meristem, a cell, or an ovule.

3. A lettuce plant, or a plant part thereof, having all of the morphological and physiological characteristics of the plant of claim 1.

4. A tissue or cell culture produced from protoplasts or cells from the plant of claim 1, wherein said cells or protoplasts are produced from a plant part selected from the group consisting of leaf, pollen, embryo, cotyledon, hypocotyl, meristem, root, root tip, pistil, anther, ovule, flower, shoot, stem, seed, stalk and petiole.

5. A lettuce plant regenerated from the tissue or cell culture of claim 4, wherein the regenerated plant has all of the morphological and physiological characteristics of cultivar ADEMPACK.

6. A method of producing a lettuce seed, wherein the method comprises crossing the plant of claim 1 with itself or a second lettuce plant.

7. The method of claim 6, wherein the method comprises crossing the plant of lettuce cultivar ADEMPACK with a second, distinct lettuce plant.

8. A lettuce seed produced by the method of claim 7.

9. A lettuce plant produced by growing the seed of claim 8.

10. A plant or seed of lettuce cultivar ADEMPACK further comprising a single locus conversion, wherein a representative sample of seed of said cultivar was deposited under ATCC Accession No. PTA-127481.

11. The plant or seed of claim 10, wherein the single locus conversion comprises a transgene.

12. The plant or seed of claim 10, wherein the single locus confers a trait selected from the group consisting of male sterility, herbicide resistance, insect resistance, pest resistance, disease resistance, modified fatty acid metabolism, modified seed yield, modified bolting, abiotic stress resistance, a value-added trait, altered seed amino acid composition, site-specific genetic recombination, and modified carbohydrate metabolism.

13. The plant or seed of claim 12, wherein the single locus confers resistance to an herbicide selected from the group consisting of glyphosate, sulfonylurea, imidazolinone, dicamba, glufosinate, phenoxy propionic acid, L-phosphinothricin, PPO inhibitors, 2,4-dichlorophenoxyacetic acid, hydroxyphenyl-pyruvate dioxygenase (HPPD) inhibitors, cyclohexone, cyclohexanedione, triazine, benzonitrile, and bromoxynil.

14. The plant or seed of claim 12, wherein the single locus comprises a transgene.

15. A method for producing a seed of a cultivar ADEMPACK-derived lettuce plant comprising the steps of:
 (a) crossing the lettuce plant of claim 1 with a second lettuce plant; and
 (b) allowing seed of an ADEMPACK-derived lettuce plant to form.

16. The method of claim 15, wherein the method further comprises the steps of:
(c) crossing a plant grown from said ADEMPACK-derived lettuce seed with itself or a second lettuce plant to yield additional ADEMPACK-derived lettuce seed;
(d) growing said additional ADEMPACK-derived lettuce seed of step (c) to yield additional ADEMPACK-derived lettuce plants; and
(e) repeating the crossing and growing steps of (c) and (d) to generate further Adempack-derived lettuce plants.

17. A method of vegetatively propagating a plant of lettuce cultivar ADEMPACK, wherein the method comprises:
(a) collecting a plant part capable of being propagated from a plant of lettuce cultivar ADEMPACK, wherein a representative sample of seed of said cultivar was deposited under ATCC Accession No. PTA-127481; and
(b) producing at least a first rooted plantlet or plant from said plant part.

18. A lettuce plantlet or plant produced by the method of claim 17, wherein the lettuce plantlet or plant has all of the physiological and morphological characteristics of lettuce cultivar ADEMPACK.

19. A method of producing a genetically modified lettuce plant, wherein the method comprises performing a technique selected from the group consisting of mutation, transformation, gene conversion, genome editing, RNA interference, and gene silencing of the plant of claim 1.

20. A method of determining a genotype of lettuce cultivar ADEMPACK, or a first-generation progeny thereof, the method comprising:
(a) obtaining a sample of nucleic acids from the plant of claim 1; and
(b) detecting a polymorphism in the nucleic acid sample.

21. A method of producing a commodity plant product, comprising obtaining the plant of claim 1, or a plant part thereof, and producing the commodity plant product from said plant or plant part thereof, wherein said commodity plant product is selected from the group consisting of fresh lettuce leaf, fresh lettuce head, cut, sliced, ground, pureed, dried, canned, jarred, washed, packaged, frozen, and heated leaves.

22. A commodity plant product produced by the method of claim 21, wherein the commodity plant product comprises at least one cell of lettuce cultivar ADEMPACK.

* * * * *